United States Patent
Marini et al.

(10) Patent No.: US 10,610,479 B2
(45) Date of Patent: *Apr. 7, 2020

(54) HYLA3D HYALURONIC ACID ACTIVATING LIP COMPLEX

(71) Applicant: Jan Marini Skin Research, San Jose, CA (US)

(72) Inventors: Jan L. Marini, San Jose, CA (US); Subhash J. Saxena, Ringoes, NJ (US)

(73) Assignee: Jan Marini Skin Research, San Jose, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/670,522

(22) Filed: Aug. 7, 2017

(65) Prior Publication Data

US 2019/0038541 A1    Feb. 7, 2019

(51) Int. Cl.
| | |
|---|---|
| *A61K 8/42* | (2006.01) |
| *A61K 8/11* | (2006.01) |
| *A61K 8/41* | (2006.01) |
| *A61Q 19/00* | (2006.01) |
| *A61K 8/68* | (2006.01) |
| *A61K 8/73* | (2006.01) |
| *A61K 8/9728* | (2017.01) |
| *A61K 8/64* | (2006.01) |
| *A61K 8/67* | (2006.01) |
| *A61K 8/9789* | (2017.01) |
| *A61K 8/02* | (2006.01) |
| *A61Q 19/08* | (2006.01) |

(52) U.S. Cl.
CPC ............ *A61K 8/735* (2013.01); *A61K 8/0216* (2013.01); *A61K 8/11* (2013.01); *A61K 8/41* (2013.01); *A61K 8/415* (2013.01); *A61K 8/42* (2013.01); *A61K 8/64* (2013.01); *A61K 8/671* (2013.01); *A61K 8/68* (2013.01); *A61K 8/9728* (2017.08); *A61K 8/9789* (2017.08); *A61Q 19/001* (2013.01); *A61K 2800/56* (2013.01); *A61Q 19/08* (2013.01)

(58) Field of Classification Search
CPC .... A61K 8/735; A61K 8/9728; A61K 8/9789; A61K 8/0216; A61K 8/11; A61K 8/41; A61K 8/415; A61K 8/42; A61K 8/64; A61K 8/671; A61K 8/68; A61Q 19/001; A61Q 19/08

USPC ........................................................ 424/401

See application file for complete search history.

(56) References Cited

U.S. PATENT DOCUMENTS

| | | |
|---|---|---|
| 6,328,987 B1 | 12/2001 | Marini |
| 6,821,524 B2 | 11/2004 | Marini |
| 8,318,678 B2 | 11/2012 | Marini |
| 9,089,505 B1 | 7/2015 | Saxena et al. |
| 9,572,767 B2 | 2/2017 | Marini et al. |
| 9,693,947 B1 | 7/2017 | Marini et al. |
| 9,808,654 B2 | 11/2017 | Marini et al. |
| 2007/0196318 A1 | 8/2007 | Marini |
| 2009/0263513 A1 | 10/2009 | Marini |
| 2010/0247693 A1 | 9/2010 | Marini |
| 2013/0189211 A1 | 7/2013 | Marini |
| 2013/0330427 A1* | 12/2013 | Smigel ............... A61K 8/97 424/725 |
| 2013/0331342 A1* | 12/2013 | Youngquist ......... C12Q 1/6837 514/20.7 |
| 2017/0000716 A1 | 1/2017 | Marini et al. |
| 2017/0056309 A1 | 3/2017 | Marini et al. |
| 2017/0258697 A1 | 9/2017 | Marini et al. |

FOREIGN PATENT DOCUMENTS

| | | |
|---|---|---|
| EP | 1203579 A1 | 5/2002 |
| EP | 1369107 A1 | 12/2003 |
| EP | 1825845 A1 | 8/2007 |
| WO | 2009/148551 A1 | 12/2009 |

* cited by examiner

*Primary Examiner* — Adam C Milligan

(74) *Attorney, Agent, or Firm* — Pamela J. Sherwood; Bozicevic, Field & Francis LLP

(57) ABSTRACT

The present invention provides cosmetic formulations for improving the appearance of the skin, particularly the lips. The compositions of the invention provide multiple enhanced technologies that work synergistically to enhance hydration and appearance of the skin. Anti-aging peptides and tissue respiratory factor work together in an HA rich environment to enhance collagen and elastin while beneficial antioxidants protect HA in the lip from damaging exposure.

12 Claims, 2 Drawing Sheets
(2 of 2 Drawing Sheet(s) Filed in Color)

HYLA3D HYALURONIC ACID ACTIVATING LIP COMPLEX

BACKGROUND

Human skin aging is a multifactorial and complex biological process affecting the different constituents of the skin. Skin aging is a combination of intrinsic or innate aging, and extrinsic aging (or photoaging) that results from exposure to environmental factors such as sunlight, pollutants, etc.

With age-skin volume, resilience, and pliability are decreased, at least in part due to altered patterns and levels of glycosaminoglycans (GAGs), especially hyaluronic acid (HA). Glycosaminoglycans and proteoglycans are abundant structural components of the extracellular matrix in addition to collagen fibers. HA forms large complexes that crosslink to other matrix proteins, such as collagen, resulting in the formation of supermolecular structures and functions to provide structure to the skin. HA has a unique capacity to bind and retain water molecules. Chemically, HA is composed of repeating polymeric disaccharides of D-glucuronic acid and N-acetyl-D-glucosamine linked by a glucuronidic β (1→3) bond. Unlike other GAGs, HA is not covalently linked to a protein core, but it may form aggregates with proteoglycans. HA polymers occur in a large number of configurations and shapes, depending on their size, salt concentration, pH, and associated cations.

In humans, HA is most abundant in the skin. The most dramatic histochemical change observed in senescent skin is the marked disappearance of epidermal HA. With increasing aging, a steady decline of HA occurs in the upper epidermal layer, with concomitant increases in the basal layer of the epidermis and the upper portions of the papillary dermis, while at senescence HA is entirely absent in the epidermis and present in the upper dermis. It is evident that during aging the epidermis loses the principal molecule responsible for binding and retaining water molecules, resulting in loss of skin moisture and accounting for some of the most striking alterations of the aged skin, including decreased structure, less support for microvessels, wrinkling, altered elasticity and loss of face volumes especially as regards to the lips.

The cosmetic formulation of the invention address specific needs of lip skin care.

SUMMARY OF THE INVENTION

The present invention provides cosmetic formulations for improving the appearance of lips. The compositions of the invention provide multiple enhanced technologies that work synergistically to enhance lip hydration, soften the appearance of upper lip lines and enhance definition. Advanced hyaluronic acid, peptides and retinol work together to improve the appearance of visible signs of aging to the lips.

According to the first aspect of the invention, there is provided a cosmetic composition comprising a specific and efficacious blend of agents, which is formulated for topical delivery to the lips, for example in a gel, cream or stick formulation. The agents include multiple forms of HA and ceramide to capture and bind water; agents that enhance endogenous HA; agents that brighten the skin and reduce the appearance of fine lines and wrinkles; and agents that enhance the volume and firmness of lips. The multiple forms of HA and ceramide comprise: liposomal encapsulated HA, which enhances delivery of large molecular weight HA deep into the skin; time-release cross-linked HA for consistent, long-term hydration; and ceramide 2 to capture and bind water for supple, smoother skin. Activating agents that boost and enhance endogenous HA comprise Tissue Respiratory Factor and palmitoyl tripeptide 38. Agents that brighten the skin and reduce the appearance of fine lines and wrinkles comprise dimethylethanolamine (DMAE), retinol, and tyramine hydrochloride.

In the second aspect of the invention, a method is provided for improving the appearance of the lips, in particular to enhance lip hydration, soften the appearance of upper lip lines and enhance definition, the method comprising applying topically to the region of the lips a cosmetic formulation comprising an efficacious blend of multiple forms of HA and ceramide to capture and bind water, comprising liposomal encapsulated HA; time-release cross-linked HA; and ceramide 2; Tissue Respiratory Factor and palmitoyl tripeptide 38 to enhance endogenous HA; dimethylethanolamine (DMAE), retinol, and tyramine hydrochloride to brighten the skin and reduce the appearance of fine lines and wrinkles.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures. The results show a dramatic change in lip and surrounding skin appearance after regular use of the product.

DETAILED DESCRIPTION OF THE EMBODIMENTS

Figure 1A:
FIG. 1A-1B show the results of use of HYLA3D activating lip complex in an individual. Shown are the baseline lip and surrounding skin condition FIG. 1A and the condition following lip complex application twice daily for 2 months FIG. 1B.

The present invention provides cosmetic formulations for improving the appearance of lips. The compositions of the invention provide multiple enhanced technologies that work synergistically to enhance lip hydration, soften the appearance of upper lip lines and enhance definition. Advanced hyaluronic acid, peptides and retinol work together to improve the appearance of visible signs of aging to the lips. The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders. The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

The compositions may be in the form of an aqueous serum or gel. These compositions are formulated according to the usual techniques as are well known to this art. The compositions of the invention may further comprise cosmetically useful agents and excipients, e.g. glycerin, cetyl alcohol, capric triglyceride, glyceryl stearate, PEG-100 stearate, steareth-20, steareth-2, cyclopentasiloxane, phenoxyethanol, lecithin, tocopherol, aloe vera, etc. each at a concentration of from about 0.1% to about 10% by weight, usually from about 0.5% to about 5%, and may be present at a concentration of from about 0.5%, 1%, 2%, 3%, 4%, 5%, etc.

COMPONENTS OF THE COSMETIC COMPOSITIONS

The compositions of the invention comprise a specific blend of therapeutic agents, including the following agents.

Forms of Hyaluronic Acid and Ceramide

Liposomal HA. Liposomal HA contains liposomally encapsulated sodium hyaluronate, which is delivered through the lipid barrier to the deeper skin layers. The product is commercially available, for example from Air Products and Chemicals, Inc., as ROVISOME®. The HA may be encapsulated, for example in lecithin, in an aqueous/alcohol diluent. In such compositions, the HA may be about 0.5% by weight, lecithin about 17.5% by weight, and the balance diluent.

The concentration of encapsulated liposomal HA may be represented in the formulation of the invention as the fraction of HA in the encapsulate, or as the finished formula concentration of the liposomal composition. When expressed as the liposomal composition, the liposomal HA may be present at a concentration of at least about 0.5%; at least about 1%; and not more than about 5%, not more than about 3%; and may be present at about 2% of the formula weight. It will be understood by one of skill in the art that the liposomal formulation comprises HA and other excipients.

Ceramide 2 (CAS 100403-19-8, N-acetyl sphingosine, Ceramide NG) is a nature identical sphingolipid that plays a key role in the establishment of the stratum corneum barrier function, thus preventing transepidermal water loss to enhance skin moisturization. It is able to capture and bind water required by the epidermis to remain supple, smooth and hydrated, and fights against skin aging and preserves the skin's youth.

The product is commercially available, for example from Sederma as Ceramide NG. Ceramide may be present at a concentration of at least about 0.01% by weight, at least about 0.03%, not more than about 0.3%, not more than about 0.1%, and may be around 0.06% formula weight.

Cross-linked HA. Crosslinked hyaluronic acid (CAS 105524-32-1) is a polymer of HA crosslinked with vinylsulfone. It has a high water-binding capacity, and is a scavenger of damaging free radicals. The polymer forms a film on the skin that is broken down over time, allowing for a sustained release of HA to the skin. Suitable compositions are commercially available, e.g. HYLASOME® EG10, from Lipo Chemicals, Inc.

The concentration of cross-linked HA may be represented as a percentage of formula weight, and may be present at a concentration of at least 0.25%, at least 0.5%, at least about 1%, and not more than about 4%, not more than about 3%; and may be present at about 2% of the formula weight.

HA Boosting Agents

Dermal Respiratory Factor. Dermal respiratory factor (Code Number: 20219PF INCI Name: Water & *Saccharomyces* Lysate Extract) comprises *Saccharomyces* cell derivative (LYCD) and *Lactobacillus* ferment. LYCD is produced when live yeast cells are exposed to stress, such as UV radiation. This yields a material which has shown to stimulate cellular metabolism by promoting the increase of cellular energy. LCYD is primarily used to stimulate oxygen consumption, combat irritation, or as a cosmetic potentiator. It has been reported to promote collagen and elastin synthesis. A commercially available source is AC Dermal Respiratory Factor Advanced PF, from Active Concepts LLC. In the composition, yeast extract is present at a concentration of 24%, and *Lactobacillus* at a concentration of 2%.

The concentration of active agent may be represented in the formulation of the invention as the fraction of LYCD, or as the finished formula concentration of the Dermal Respiratory Factor composition. When expressed as the concentration of Dermal Respiratory Factor formulation present in the cosmetic formulation of the invention, the respiratory factor may be present at a concentration of at least about 0.05%; at least about 0.1%; and not more than about 1%, not more than about 0.5%; and may be present at about 0.25% of the formula weight. It will be understood by one of skill in the art that the Dermal Respiratory Factor formulation comprises aqueous diluents in addition to the microbial cell extracts.

Palmitoyl tripeptide 38 (CAS 1101175-36-3) is a tripeptide having the formula Pal-KMO$_2$K, which derived from naturally occurring peptide motifs in collagen and laminins. It has been reported to stimulate the synthesis of matrix and dermal-epidermal junction molecules. Suitable compositions are commercially available, e.g. VOLULIP™, from Sederma, which formulates palmitoyl tripeptide 38 with extract of *Portulaca pilosa* and liposoluble excipients. In such compositions, the tripeptide is present at about 0.05% of the composition.

The concentration of palmitoyl tripeptide 38 may be represented in the formulation of the invention as the fraction of palmitoyl tripeptide 38, or as the finished formula concentration of the VOLULIP™ composition. When expressed as formula weight of VOLULIP™, the concentration of at least about 0.25%; at least about 0.5%; and not more than about 2.5%; and may be present at about 1% of the formula weight. It will be understood by one of skill in the art that the VOLULIP™ composition comprises extract of *Portulaca pilosa* and other excipients. The tripeptide itself may be present at a concentration in the total formulation of about 0.0001% to 0.001% by weight, and may be present at around about 0.0005% by weight. When present, extract of *Portulaca pilosa* may be present at a concentration of at least about 0.01% and not more than about 0.05%, and may be present at a concentration of around about 0.02%.

Skin Brightening Agents

Retinol, CAS #68-26-8, (2E,4E,6E,8E)-3,7-dimethyl-9-(2,6,6-trimethylcyclohex-1-enyl) nona-2,4,6,8-tetraen-1-ol, may be present at a concentration of from 0.01%, of from around 0.05% to about 0.5%, and may be about 0.1% by weight.

Dimethylethanolamine (DMAE, CAS 108-01-0) is an anti-inflammatory, antioxidant ingredient with pH buffering properties. It has been reported to increase firmness of the skin and fullness of the lips. It is widely available commercially.

The concentration of DMAE may be represented as a percentage of formula weight, and may be present at a concentration of at least 0.25%, at least 0.5%, and not more than about 3%, not more than about 2%; and may be present at about 1% of the formula weight.

Tyramine hydrochloride (4-(2-Aminoethyl)phenol hydrochloride, CAS 60-19-5) is a naturally-occurring monoamine derived from the amino acid tyrosine. It is widely available commercially.

The concentration of tyramine hydrochloride may be represented as a percentage of formula weight, and may be present at a concentration of at least 0.25%, at least 0.5%, and not more than about 3%, not more than about 2%; and may be present at about 0.9% of the formula weight.

The amounts of cosmetic or dermatological auxiliaries and additives and perfume to be used in each case can easily be determined by simple exploratory experiments by the person skilled in the art, depending on the nature of the product in question. Preferably the compositions of the invention are fragrance free and paraben-free.

COSMETICALLY ACCEPTABLE VEHICLE

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The compositions of the invention include a cosmetically acceptable vehicle to act as a diluent, dispersant or carrier for the active agents, so as to facilitate distribution and uptake when the composition is applied to the region of the lips. Vehicles other than or in addition to water, triglycerides, glycerol, etc. can include liquid or solid emollients, solvents, humectants, thickeners and powders. The cosmetically acceptable vehicle will usually form 5% to 99.9%, preferably from 25% to 80%, about 40% to 60%, by weight of the composition, and can, in the absence of other cosmetic adjuncts, form the balance of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention comprises a cream suitable for administration to the lips. Furthermore, a composition of the invention may include additional agents or additives that are not in themselves active agents but play a role in promoting the usefulness or effectiveness of an active agent.

PRODUCT USE, FORM, AND PACKAGING

In use, a quantity of the composition, for example from 1 to 100 ml, is applied to the lips from a suitable container or applicator and, if necessary, it is then spread over and/or rubbed into the site using the hand or fingers or a suitable device.

The cosmetic composition of the invention can be formulated in any form suitable for application to the lips, including a lotion, cream, gel, stick, or the like. The composition can be packaged in any suitable container to suit its viscosity and intended use by the consumer. For example, a lotion or cream can be packaged in a bottle or tube. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates a topical composition according to the present invention. The composition can be processed in conventional manner and is suitable for cosmetic use. In particular the compositions are suitable for application to a site of interest for the treatment of a variety of skin conditions.

HYLA3D Complex

| CAS number | Name | Final concentration by weight |
|---|---|---|
| 9067-32-7 | Encapsulated, liposomal Sodium Hyaluronate | 0.5%-3% |
| 105524-32-1 | Sodium Hyaluronate Crosspolymer | 0.5%-3% |
| 100403-19-8 | Ceramide 2 | 0.01%-0.1% |
|  | Dermal Respiratory Factor | 0.05%-0.5% |
| 1101175-36-3 | Palmitoyl tripeptide 38 | 0.25%-2.5%* |
| 68-26-8 | Retinol | 0.01%-0.5% |
| 108-01-0 | Dimethylethanolamine | 0.25%-3% |
| 60-19-5 | Tyramine hydrochloride | 0.25%-2% |

*expressed as percentage of VOLULIP™ present in formulation.

Additional ingredients can be included to provide a cosmetically acceptable vehicle and to bring the volume to 100%, comprising one or more of Alcohol, Amigel Granulated, Aqua (Water), BHA*, BHT*, Calcium Gluconate*, Cetearyl Ethylhexanoate, Cetyl Alcohol, Citric Acid (40% Aq. Sol.), Co Enzyme Q10 (Ubiquinone), Disodium EDTANersene NA2, DL-Alpha-Tocopheryl Acetate, Gluconolactone, Glycerin, Glyceryl Stearate, Hexyl Laurate, Hydrogenated Castor Oil, PEG 20 Stearate (LIPOPEG 10-S), Pentylene Glycol*, Polyacrylate Crosspolymer-6, Polysorbate 20, *Portulaca Pilosa* Extract, Potassium Phosphate, Ricinus Communis (Castor) Seed Oil, Sodium Benzoate, Sodium Saccharin, Sorbitan Isostearate, Sorbitan Stearate, Sorbitol, Sucrose Cocoate, t-Butyl Alcohol*, Titanium Dioxide USP (MPSI #3328), Xanthan Gum.

Figure 1B:
Figure 2A:
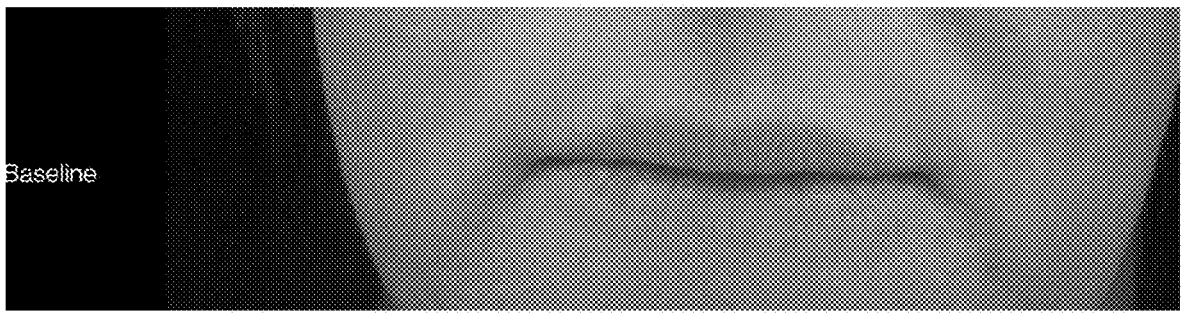
FIG. 2A-2B show the results of use of HYLA3D activating lip complex in a second individual, showing baseline FIG. 2A and following lip complex application twice daily for 1 month FIG. 2B.
Figure 2B:
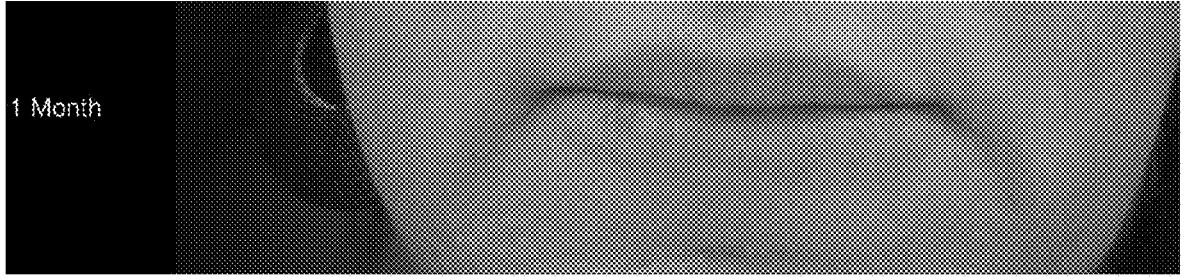
Figure 3A:
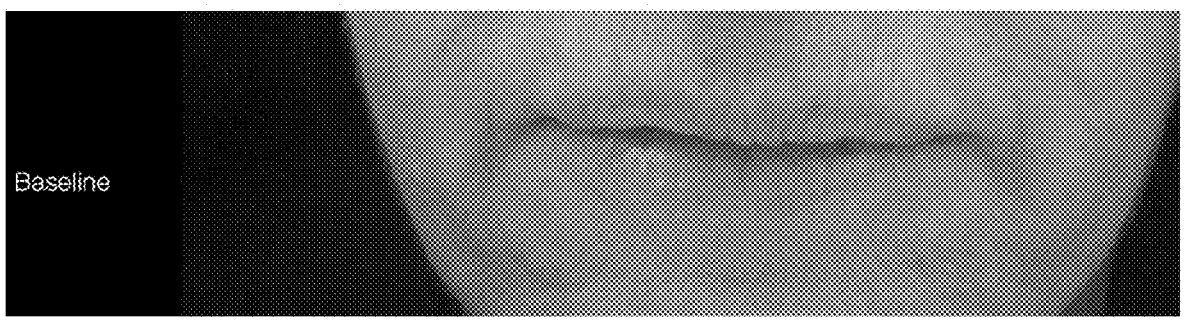
FIG. 3A-3D show the results of use of HYLA3D activating lip complex in a second individual, showing baseline FIG. 3A and following lip complex application twice daily for 2, 3 and 4 months, respectively FIG. 3B-3D.
Figure 3B:
Figure 3C:
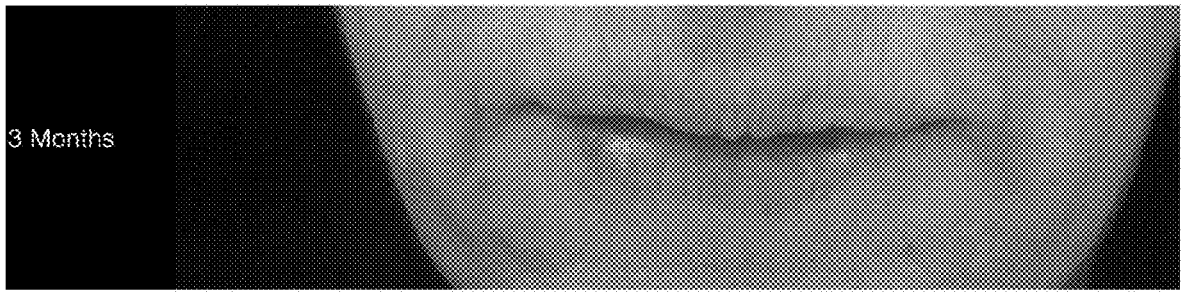
Figure 3D:

As shown in FIGS. 1-3, twice daily use of the topical composition over a period of from 1 to 4 months provides for improved appearance of the lips and surrounding region.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application to improve appearance of the lips comprising:
   a blend of hyaluronate, ceramide and endogenous hyaluronic acid activating ingredients comprising:
   0.5% to 5% by total weight encapsulated sodium hyaluronate; 0.25% to 3% by total weight sodium hyaluronate crosspolymer; 0.01% to 0.3% by total weight ceramide 2; 0.05% to 1% by total weight dermal respiratory factor wherein the dermal respiratory factor comprises 24% *Saccharomyces* cell derivative, 2% *Lactobacillus* ferment and water; and 0.0001% to 0.001% by total weight palmitoyl tripeptide 38; and
   a cosmetically acceptable vehicle.

2. The composition of claim 1, further comprising:
   0.05% to 0.5% by total weight retinol; 0.5% to 3% by total weight dimethylethanolamine; and 0.25% to 3% by total weight tyramine hydrochloride.

3. The composition of claim 1, wherein the blend of hyaluronate, ceramide and endogenous hyaluronic acid activating ingredients comprises:
   1% to 3% by total weight encapsulated sodium hyaluronate; 1% to 3% by total weight sodium hyaluronate crosspolymer; 0.03% to 0.1% by total weight ceramide 2; 0.1% to 0.5% by total weight dermal respiratory factor; and 0.0001% to 0.001% by total weight palmitoyl tripeptide 38.

4. The composition of claim 2, wherein the concentrations of retinol, dimethylethanolamine and tyramine hydrochloride are:

0.05% to 0.5% by total weight retinol; 0.5% to 2% by total weight dimethylethanolamine; and 0.5% to 2% by total weight tyramine hydrochloride.

5. The composition of claim 4, wherein the palmitoyl tripeptide 38 is provided with extract of *Portulaca pilosa* at a concentration of from 0.01% to 0.05% by total weight.

6. The composition of claim 5, formulated as a cream.

7. A method of improving the appearance of the lips, comprising:

topically applying to the lips the cosmetic composition of claim 1.

8. The method of claim 7, wherein the cosmetic composition further comprises:

0.05% to 0.5% by total weight retinol; 0.5% to 3% by total weight dimethylethanolamine; and 0.25% to 3% by total weight tyramine hydrochloride.

9. The method of claim 8, wherein the blend of hyaluronate, ceramide and endogenous hyaluronic acid activating ingredients comprises:

1% to 3% by total weight encapsulated sodium hyaluronate; 1% to 3% by total weight sodium hyaluronate crosspolymer; 0.03% to 0.1% by total weight ceramide 2; 0.1% to 0.5% by total weight dermal respiratory factor; and 0.0001% to 0.001% by total weight palmitoyl tripeptide 38.

10. The method of claim 8, wherein the concentrations of retinol, dimethylethanolamine and tyramine hydrochloride are:

0.05% to 0.5% by total weight retinol; 0.5% to 2% by total weight dimethylethanolamine; and 0.5% to 2% by total weight tyramine hydrochloride.

11. The method of claim 10, wherein the palmitoyl tripeptide 38 is provided with extract of *Portulaca pilosa* at a concentration of from 0.01% to 0.05% by total weight.

12. The method of claim 11, wherein the cosmetic composition is formulated as a cream.

* * * * *